United States Patent [19]
Taha et al.

[11] Patent Number: 5,952,280
[45] Date of Patent: *Sep. 14, 1999

[54] AGGLOMERATED CLAY CARRIER WITH AN ANTIBACTERIAL AGENT FOR LAUNDRY APPLICATIONS

[75] Inventors: Riad Ahmed Taha, Spotswood; Patrick J. Getty, Metuchen, both of N.J.

[73] Assignee: Colgate-Palmolive Co., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/918,786

[22] Filed: Aug. 25, 1997

Related U.S. Application Data

[63] Continuation-in-part of application No. 08/898,664, Jul. 22, 1997, abandoned.

[51] Int. Cl.[6] .............................. C11D 1/66; C11D 3/24; C11D 3/48
[52] U.S. Cl. ..................... 510/319; 510/276; 510/382; 510/515; 510/334; 510/444; 510/349; 510/443; 510/507
[58] Field of Search ..................................... 510/507, 443, 510/334, 444, 515, 319, 276, 382, 349, 471; 119/169, 171, 173; 424/49, 54, 57, 52

[56] References Cited

U.S. PATENT DOCUMENTS

| | | | |
|---|---|---|---|
| 4,494,482 | 1/1985 | Arnold | 119/1 |
| 5,011,602 | 4/1991 | Totani et al. | 210/484 |
| 5,332,513 | 7/1994 | Doms et al. | 252/8.6 |
| 5,478,563 | 12/1995 | Erami | 424/409 |

FOREIGN PATENT DOCUMENTS

| | | | |
|---|---|---|---|
| 9-020603 | 1/1997 | Japan | A01N 31/08 |
| 9-194899 | 7/1997 | Japan | C11D 17/06 |

*Primary Examiner*—Yogendra Gupta
*Assistant Examiner*—Gregory E. Webb
*Attorney, Agent, or Firm*—Bernard Lieberman

[57] ABSTRACT

A particulate agglomerated carrier is described which is suitable for use in admixture with a laundry detergent composition and which is capable of depositing an effective amount of an antibacterial agent on laundered fabrics and for providing an effective amount of same in the wash solution. The carrier is an agglomerate of a smectite-type clay and an antibacterial agent.

Also, described is a laundry detergent composition containing such agglomerated carrier and process for depositing an effective amount of an antibacterial agent on laundered fabrics and for providing an effective amount of such antibacterial agent in the wash solution.

18 Claims, No Drawings

AGGLOMERATED CLAY CARRIER WITH AN ANTIBACTERIAL AGENT FOR LAUNDRY APPLICATIONS

BACKGROUND OF THE INVENTION

This application is a continuation-in-part of prior application Ser. No. 08/898,664 filed Jul. 22, 1997, now abandoned, the disclosure of which is incorporated herein by reference.

FIELD OF THE INVENTION

This invention relates to agglomerated carrier particles containing a smectite- type clay and an antibacterial agent. More particularly, it relates to the use of such agglomerated particles as a component of a laundry detergent composition or as an additive to the wash solution for depositing an effective amount of antibacterial agent on laundered fabrics and for providing an effective amount of such antibacterial agent in the wash solution.

DESCRIPTION OF RELATED ART

The combination of an antibacterial agent with a particulate carrier material to provide an antibacterial composition capable of sterilizing or inhibiting the growth of bacteria in a liquid or on a solid surface is extensively described in the patent literature. In U.S. Pat. No. 5,011,602 there is described what is referred to as an antibacterial material for water which is used to sterilize water and which is comprised of an antibacterial agent bound or adsorbed on a carrier. Activated clay is listed among the suitable carriers. In U.S. Pat. No. 5,478,563 there is described "an easily condensable antibacterial agent" which is adsorbed on a carrier such as zeolite or clay among numerous other listed materials, and the resulting particulate carrier then blended with a described plastic resin to provide an antibacterial polyacetal resin composition. In U.S. Pat. No. 4,081,267, bentonite clay is exemplified as a carrier for a described herbicide and fungicide to provide herbicidal activity in plants.

The use of DCMX (dichloro meta xylenol) as a bacteriostat on a clay carrier is described in U.S. Pat. No. 4,494,482 to provide an animal litter product intended to control odor development.

Agglomerated particles of bentonite are well-known additives for detergent compositions to provide fabric softening effects to laundry. U.S. Pat. No. 4,767,546 to Weinstein describes the agglomeration of bentonite powder in an agglomerator using an aqueous solution of sodium silicate as the binder liquid. The resulting agglomerates are used in laundry detergent compositions. In U.S. Pat. No. 4,536,315 particles of a smectite-type clay are used as a carrier for a perfume which is adsorbed on the clay particles. The perfume-containing carrier is intended for use in admixture with a laundry detergent composition to impart a pleasing fragrance to laundered fabrics. In U.S. Pat. No. 4,609,473 to Ramachandran et al. agglomerated particles of bentonite and sodium sulfate are described which provide improved fabric softening effects to washed laundry. The patent also provides a list of non-interfering adjuvants which may be incorporated with the bentonite-sulfate agglomerates, among which are perfumes and antibacterial compounds.

In U.S. Pat. No. 5,332,513 to Doms et al. bentonite powder agglomerates are described wherein the bentonite is agglomerated with a co-melt of pentaerythritol ditallowate (PEDT) and a nonionic surfactant. The resulting fabric softening agglomerated particles may be added to a wash or rinse water or preferably incorporated into a particulate laundry detergent composition to provide fabric softening activity to laundered fabrics.

SUMMARY OF THE INVENTION

The present invention provides a particulate agglomerated carrier which is an agglomerate of a smectite-type clay and an antibacterial agent, which carrier is suitable for use in admixture with a laundry detergent composition or as an additive to a wash solution separate from any detergent composition, and which carrier is capable of depositing an effective amount of said antibacterial agent on laundered fabrics, said carrier being comprised of
(a) finely divided particles of said smectite-type clay; and
(b) an antibacterial agent which is normally solid at ambient temperature, wherein said particles of smectite-type clay are agglomerated at a temperature above ambient with a melt of said antibacterial agent to form an agglomerated mixture which can be reduced in size to the range of particle size desired for said particulate carrier.

In accordance with the process aspect of the invention antibacterial activity is provided to laundered fabrics by contacting such fabrics during a laundering operation with wash water or rinse water containing dispersed therein the above-defined particulate agglomerated carrier.

The process of the invention can be conveniently carried out in a washing machine during laundering or by contact of the fabrics with a wash solution or rinse solution during hand washing.

The term "antibacterial agent" as used herein refers to materials which prevent or inhibit the growth of bacteria on an inanimate surface.

Among the known antibacterial agents which are suitable for the present invention are phenolic and xylenol antibacterial agents. Two are particularly preferred: PCMX (para chlorometa xylenol) and triclosan (2,4,4'-trichloro-2'-hydroxy diphenyl ether). These are normally solid at room temperature and have melting points of about 115° C. for PCMX and about 50° C. for triclosan.

Other useful antibacterial agents include 3,4,4'-trichloro carbanilide, DTBBP (2,t-butyl-4-cyclohexylphenol) and other suitable antibacterial compounds containing phenol groups. Also useful herein are oxidants such as sodium perborate, activated perborate, percarbonate and the like.

Less preferred for the present invention are those antibacterial agents such as quaternary ammonium compounds which are generally incompatible with certain detergent ingredients such as anionic surfactants.

DETAILED DESCRIPTION OF THE INVENTION

The particulate agglomerated carriers of the invention are suitable as additives to or as components of a granular or liquid detergent composition or alternatively they may be used to provide antibacterial effects to washed laundry by adding the agglomerated carrier to the wash solution separately from the detergent composition such as, for example, during the wash cycle or rinse cycle of a washing machine. The agglomerated carrier is comprised of finely divided smectite-type clay, preferably bentonite, having particle sizes less than about 75 microns, which is agglomerated to particles in the particle size range of 150 to 850 microns.

The agglomerated carrier is added to the wash solution in an amount to provide a dosage of from about 0.1 to 2 g/liter, perferably 0.5 to 1.0 g/liter.

The smectite-type clays, such as bentonite, are colloidal clays containing montmorillonite. Montmorillonite is a hydrated aluminum silicate in which about ⅙th of the aluminum atoms may be replaced with magnesium atoms. Atom substitution by iron, sodium, potassium, calcium, magnesium and other metals can occur within the crystal lattice of the smectite clays. It is customary to distinguish between clays on the basis of their predominant cation. For example, a sodium clay is one in which the cation is predominantly sodium. With regard to the present carriers, the predominant cation in the aluminum silicate lattice may be either sodium or calcium.

Preferred bentonites for purposes of the invention are sold by Colin Stewart, Inc. of Cheshire, England. Equivalent competitive products are sold by American Colloid Company.

The preparation of the agglomerated carriers of the invention requires that the antibacterial agent be first heated above ambient to its melting point, following which the molten anti-bacterial agent is mixed by conventional means with the clay powder to form an agglomerated mixture. The weight ratio of clay to antibacterial agent is generally from about 15:1 to about 5:1 and preferably about 10:1. To insure the uniformity of the clay/antibacterial agent agglomerate, water is preferably added to the agglomerated mixture to create a slurry which is agitated and then allowed to dry, preferably in an oven, to create a uniform dried agglomerated mixture. This agglomerate is then conveniently size-reduced manually or in a conventional size- reducing apparatus to produce agglomerated particles having particle sizes in the desired range, generally from about 150 to 850 microns.

The agglomerated particles of the invention may also advantageously include a softening ingredient such as a higher fatty acid ester of pentaerythritol, a higher fatty acid ester of pentaerythritol oligomers or a higher fatty acid ester of lower alkylene oxide derivatives of pentaerythritol. Pentaerythritol compound may be abbreviated as PEC herein, which description and abbreviation may apply to any or all of pentaerythritol, oligomers thereof and alkoxylated derivatives thereof, as such, or more preferably and more usually, as the esters, as may be indicated by the context.

The oligomers of pentaerythritol are preferably those of two to five pentaerythritol moieties, more preferably 2 or 3, with such moieties being joined together through etheric bonds. The lower alkylene oxide derivatives thereof are preferably of ethylene oxide or propylene oxide monomers, dimers or polymers, which terminate in hydroxyls and are joined to the pentaerythritol or oligomer of pentaerythritol through etheric linkages. Preferably there will be one to ten alkylene oxide moieties in each such alkylene oxide chain, more preferably 2 to 6, and there will be one to ten such groups on a PEC, depending on the oligomer. At least one of the PEC OH groups and preferably two, are esterified by a higher fatty acid or other higher aliphatic acid, which can be of an odd or even number of carbon atoms.

The higher fatty acid esters of the pentaerythritol compounds are preferably partial esters and more preferably there will be at least two free hydroxyls thereon after esterification (on the pentaerythritol, oligomer or alkoxyalkane groups). Frequently the number of such free hydroxyls is two or about two but sometimes it may be one, as in pentaerythritol tristearate, or as many as eight, as in penta-pentaerythritol tetrapalmitate.

The higher aliphatic or fatty acids that may be employed as esterifiing acids are those of carbon atom contents in the range of 8 to 24, preferably 12 to 22 and more preferably 12 to 18, e.g., lauric, myristic, palmitic, oleic, stearic and behenic acids. The fatty acids may be mixtures of such fatty acids, obtained from natural sources, such as tallow or coconut oil, e.g., pentaerythritol ditallowate (the tallow acids diester of pentaerythritol, PEDT) or from such natural materials that have been hydrogenated. Synthetic acids of odd or even numbers of carbon atoms may also be employed. Of the aforementioned fatty acids, lauric, stearic , coco and tallow acids are often preferred (and such preference may depend on the pentaerythritol compound being esterified).

The addition of a PEC compound as described above to the agglomerated carrier of the invention is conveniently carried out by heating the PEC compound to its melting point and then mixing the molten PEC compound with the particles of the invented agglomerated carrier to form a pasty mass which is allowed to dry and then size reduced by conventional means to the desired particle size range.

As noted above, the agglomerated carrier of the invention may be conveniently incorporated in a laundry detergent composition. The active detergent in such a laundry detergent composition is desirably either an anionic surfactant or a nonionic surfactant or a mixture of such surfactants. A mixture of surfactants is often preferred from the standpoint of efficient cleaning.

Suitable anionic surfactants include the water-soluble alkali metal salts having alkyl radicals containing from about 8 to about 22 carbon atoms, the term alkyl being used to include the alkyl portion of higher acyl radicals. Examples of suitable synthetic anionic detergent compounds are sodium and potassium alkyl sulphates, especially those obtained by sulphating higher ($C_8$–$C_{18}$) alcohols produced, for example, from tallow or coconut oil; sodium and potassium alkyl ($C_9$–$C_{20}$) benzene sulfonates, particularly sodium linear secondary alkyl ($C_{10}$–$C_{15}$) benzene sulfonates; sodium alkyl glycerol ether sulfates, especially those ethers of the higher alcohols derived from tallow or coconut oil and synthetic alcohols derived from petroleum; sodium coconut oil fatty monoglyceride sulfates and sulfonates; sodium and potassium salts of sulfuric acid esters of higher ($C_8$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and potassium salts of fatty acid amides of methyl taurine; alkane monosulfonates such as those derived from reacting alpha-olefins ($C_8$–$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$–$C_{20}$ alpha-olefins, with $SO_3$ and then neutralizing and hydrolyzing the reaction product. The preferred anionic surfactants are ($C_{10}$–$C_{18}$) alkyl polyethoxy (1–11 Eo) sulfates and mixtures thereof having differing water solubilities.

Suitable nonionic surfactants include, in particular, the reaction products of compounds having a hydrophobic group and a reactive hydrogen atom, for example aliphatic alcohols, acids, amides and alkyl phenols with alkylene oxides, especially ethylene oxide, either alone or with propylene oxide. Specific nonionic surfactant compounds are alkyl ($C_6$–$C_{18}$) primary or secondary linear or branched alcohols condensed with ethylene oxide, and products made by condensation of ethylene oxide with the reaction products of propylene oxide and ethylenediamine. Other so-called nonionic surfactant compounds include long chain tertiary amine oxides, long-chain tertiary phosphine oxides, dialkyl sulfoxides, fatty ($C_8$–$C_{18}$) esters of glycerol, sorbitan and the like, alkyl polyglycosides, ethoxylated glycerol esters, ethoxylated sorbitans and ethoxylated phosphate esters.

The preferred non-ionic surfactant compounds are those of the ethoxylated and mixed ethoxylated-propyloxylated ($C_6$–$C_{18}$) fatty alcohol type, containing 2–11 EO groups.

Examples of amphoteric surfactants which can be used in the compositions of the present invention are betaines and those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isothionate, N-higher alkyl aspartic acids and the products sold under the trade name "Miranol".

Examples of betaines useful herein include alkylamido betaines, alkylamino betaines, alkyl betaines and sulfobetaines. The high alkyl betaines are represented by coco dimethyl carboxymethyl betaine, lauryl dimethyl carboxymethyl betaine, lauryl dimethyl alpha-carboxymethyl betaine, cetyl dimethyl carboxymethyl betaine, lauryl bis(2-hydroxyethyl) carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxymethyl betaine, etc. The sulfo-betaines may be represented by coco dimethyl sulfopropyl betaine, stearyl dimethyl sulfopropyl betaine, lauryl bis-(2-hydroxyethyl) sulfopropyl betaine, amino betaine amidosulfobetaines, and the like.

Other suitable betaines include 1-(lauryl, dimethylammonio) acetate-l-(myristyl dimethylammonio) propane-3-sulfonate, 1-(myristyl dimethylamino)-2-hydroxypropane-3-sulfonate, cocoamidoethylbetaine and cocoamidopropylbetaine.

An especially preferred class of amphoteric surfactants are the glycinate derivatives of the formula:

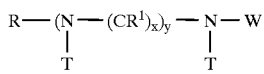

wherein R is a hydrocarbon group, preferably a $C_8$ to $C_{20}$ aliphatic, $R^1$ is hydrogen or a $C_1$ to $C_6$ alkyl, preferably hydrogen or methylene, T is hydrogen or W, preferably W, W is $R^2COOM$ wherein M is hydrogen, alkali metal, alkaline earth metal, ammonium or substituted ammonium, such as lower alkanolamine, e.g., triethanolamine, x is 2 to 3 and y is 2 to 4, and $R^2$ is a $C_1$ to $C_6$ alkylene. A preferred amphoteric surfactant is of the formula

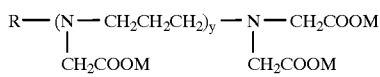

wherein R is an aliphatic hydrocarbon group, preferably a $C_{16}$ to $C_{18}$ fatty alkyl or fatty alkylene, M is alkali metal, and y is 3 to 4. More preferably R is tallowalkyl (which is a mixture of stearyl, palmityl and oleyl in the proportions in which they occur in tallow), M is sodium and y is about 3.5, representing a mixture of about equal parts of the amphoteric surfactant wherein y is 3 and such amphoteric surfactant wherein y is 4. Preferred amphoteric surfactants of this type are available commercially under the trade name Ampholak™ 7TX obtainable from Kenobel AB, a unit of Nobel Industries, Sweden.

The total amount of surfactant in the composition will generally range from about 5% to about 75%, more usually from about 5% to about 30%. In the event that a mixture of anionic and non-anionic surfactants is used herein, the anionic surfactant is preferably at least 40% by weight of such mixture.

The nonionic surfactant is used in an amount of from about 0.5 to 15%, preferably from about 1 to 10% by weight and the amphoteric surfactant when present, can comprise from about 0.3 to 15%, preferably 1 to 10%, most preferably from about 1 to 8% by weight, based on the total composition.

Cationic surfactants which maybe used include mono $C_8$–$C_{24}$ alkyl or alkenyl onium salts, especially mono-or polyammonium salts, imidazolinium salts, pyridinium salts or mixtures thereof. Especially preferred cationics include the following: stearyldimethylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylisoquinolium bromide; ditallow-(hydrogenated) dimethyl ammonium chloride; dilauryldimethyl ammonium chloride; and stearalkonium chloride.

A more detailed illustration of the various surfactants and classes of surfactants mentioned may be found in the text *Surface Active Agents,* Vol. II, by Schwartz, Perry and Berch (Interscience Publishers, 1958), in a series of annual publications entitled *McCutcheon's Detergents and Emulsifiers,* issued in 1969, or in *Tenside-Taschenbuch,* H. Stache, 2nd Ed. Carl Hanser Verlag, Munich and Vienna, 1981.

The composition may also contain one or more detergency builders. Preferred builders include organic builders, for example, polycarboxylate builders, such as aminopolycarboxylates, for example, sodium and potassium ethylene-diamine tetraacetate; sodium and potassium nitrotriacetate; and the polyacetal polycarboxylates, such as those described, for example, in U.S. Pat. Nos. 4,144,226 and 4,315,092. Other organic builders of the polycarboxylate type include the water-soluble salts, especially sodium and potassium salts, of mellitic acid, citric acid, pyromellitic acid, benzene polycarboxylic acids, carboxymethyloxy succinic acid, cis-cyclohexane hexacarboxylic acid, and the like. Citric acid salt, e.g., potassium or sodium citrate, is often a preferred builder in non-phosphate or low phosphate formulations. In liquid detergent compositions, the citric acid salt also serves a dual function as a builder and an electrolyte which helps maintain the surfactant micelles dispersed in the aqueous liquid medium.

Conventional builders which may be used include phosphates such as alkali metal polyphosphates, and alkali or alkaline earth metal silicates, carbonates, and bicarbonates, as well as water-insoluble aluminosilicate zeolite, such as zeolite A. Sodium tripolyphosphate is especially preferred but other phosphate builders such as tetrasodium pyrophosphate can also be used. Mixtures of sodium tripolyphosphate and sodium carbonate as disclosed in U.S. Pat. No. 4,842,769 are also useful.

The zeolites useful in the present invention include the crystalline, amorphous and mixed crystalline-amorphous zeolites of either natural or synthetic origin. It is preferred that the zeolites rapidly and effectively counteract hardness cations, such as calcium, magnesium, iron and the like to soften the wash water before such hardness ions adversely react with any other components of the detergent composition.

The preferred zeolites have a high calcium ion exchange capacity, normally from about 200 to 400 or more, milliequivalents of calcium carbonate hardness per gram of the aluminosilicate ("meq./g."). It is preferred that the zeolite used has a calcium capacity between about 250 to 350 meq./g.

Although other ion exchanging zeolites may also be utilized, the finely divided synthetic zeolite builder particles preferred in the practice of this invention will have the formula

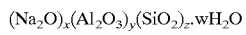

$$(Na_2O)_x(Al_2O_3)_y(SiO_2)_z \cdot wH_2O$$

wherein x is 1, y is from 0.8 to 1.2 (preferably about 1), z is from 1.5 to 3.5 (preferably 2 to 3, and more preferably about 2) and w is from 0 t 9 (preferably 2.5 to 6).

The water insoluble crystalline aluminosilicates used are often characterized by having a network of substantially uniformly sized pores in the range of about 3 to 10 Angstroms, often being about 4 Å (normal). This size is determined by the unit structure of the zeolite crystal. The zeolite should be an univalent cation-exchanging zeolite, i.e., it should be an aluminosilicate of an univalent cation such as sodium, potassium, lithium (when practicable) or other alkali metal, ammonium or hydrogen. Preferably, the univalent cation of the zeolite molecular sieve is an alkali metal cation, preferably sodium or potassium and most preferably sodium. However, other cations are also useful.

Crystalline zeolites that are good ion exchangers for use in the invention, at least in part, include zeolites of the following crystalline structure groups: A, X, Y, L, mordenite and erionite. The A, X and Y types are preferred. These crystalline types of zeolites are well-known in the art and are described in Zeolite Molecular Sieves by Donald W. Beck, published in 1974 by John Wiley & Sons. Typical commercially available zeolites of the types mentioned above are listed in Table 9.6, at pages 747–749, of the Beck text, which table is incorporated herein by reference.

The detergent composition may also contain one or more enzymes which are active against biodegradable stains, e.g., starches, vegetable and blood. Preferred enzymes which may be used include amylolytic enzymes (alpha amylases), alkaline and neutral proteases, lipolases, cellulases and the like, and mixtures thereof Where used, the enzymes are normally present in the detergent composition at a level of from about 0.01 up to about 5 wt %, more preferably from about 0.1 to 2 wt %.

The composition may also contain a suitable stabilizer system for the enzyme such as up to 1 wt % calcium chloride or the combination of boric acid, boric oxide or alkali metal borate and water soluble calcium salt.

An optional, but often preferred additive, is a higher fatty acid, which may be saturated or unsaturated, and may contain from about 10 to about 22 carbon atoms, preferably from about 12 to 20 carbon atoms. Oleic acid is especially preferred in amounts of from 0.1 to about 10% by weight of the composition. These higher fatty acids function in the detergent compositions as anti-foaming agents and also function as soap surfactants in combination with neutralizing cations, e.g., sodium or potassium, present in the composition. They may be used alone for this anti-foaming function but are often used in combination with polysiloxane (silicone) anti-foaming agents. The silicone anti-foaming agents will generally be present in minor amounts compared to the fatty acid. Suitable ratios (by weight) of the fatty acid anti-foaming agent to silicone anti-foaming agent may range from about 100:1 to 1:10, preferably 50:1 to 1:1, especially 30:1 to 2:1.

Other conventional materials may also be present in the liquid detergent compositions of the invention, for example, soil-suspending agents, thickening agents, sequesterants such as salts of ethylene diamine tetraacetic acid or analogous phosphonic acid salts, hydrotropes, corrosion inhibitors, dyes, perfumes, optical brighteners, suds boosters, germicides, e.g., quaternary ammonium salts, preservatives, e.g., quaternium 15, anti-tarnishing agents, opacifiers, oxygen-liberating bleaches such as sodium perborate or percarbonate with or without bleach precursors, buffers and the like. Such other conventional materials may be used in the amounts they are normally used generally up to about 5% by weight, more preferably up to about 3% by weight, although higher amounts which do not interfere with the stability of the composition or give rise to an unacceptably high pH may be used, if desired.

The detergent compositions useful in combination with the present invention may be in liquid or in granular form. The liquid carrier for the liquid compositions of this invention is preferably water alone, but an aqueous carrier containing minor amounts of a lower alcohol, such as ethanol or isopropanol, may also be used in some cases. Generally, water levels may be up to about 90% by weight of the composition, for example, from about 20% to about 90%, preferably from about 20% to 70%, by weight. The water may be deionized, but usually tap water is sufficient.

The viscosity of the liquid detergent composition is normally in the range of about 800 to 10,000 centipoises, preferably 2,000–7,000 centipoises, but products of other suitable viscosities may also be useful. At the viscosities mentioned, the liquid detergent is pourable, stable, nonseparating and uniform.

Powder or granular forms of the detergent composition may be prepared by conventional granulation techniques, such as spray drying, wherein a liquid formulation (crutcher slurry) is spray dried and the resulting granular product collected. The crutcher slurry also preferably will contain one or a mixture of granulation aids such as sodium sulfate, silicates, clays and other well known material as such as disclosed in U.S. Pat. Nos. 5,024,778 and 5,332,513. The amount of such granulation aids will generally range from about 10 to 50 wt %. The water content of such granular detergents generally ranges from about 5 to 15 wt %.

EXAMPLE 1

Preparation of Agglomerated Carrier

Agglomerated carrier particles in accordance with the invention were prepared as follows using PCMX as the antibacterial agent and bentonite clay purchased from Colin-Stewart Inc. as the smectite clay.

Into a 100 ml glass beaker there was added 25 g of PCMX in solid granular form. The beaker was heated using a hot plate until the PCMX was melted and in liquid form. Two-hundred grams of powdered bentonite having a minimum of 95% of particles finer than 100 mesh or 150 microns in diameter was introduced into a 1,500 ml glass beaker. Twenty grams of melted PCMX was then poured onto the bentonite, and a large spatula was used to manually mix the PCMX and clay. The weight ratio of clay:PCMX was 10:1. Deionized water was gradually added in increments to the clay/PCMX mixture while mixing until about 500 grams of water was finally added; an amount sufficient to create a slurry.

After formation of the slurry, the 1,500 ml beaker was placed in a microwave oven for intervals of 1–2 minutes for drying. After each drying interval, the beaker was removed from the microwave oven and allowed to cool for a period of about 5 minutes during which time the slurry was thoroughly mixed using a spatula. Drying in this manner in the microwave oven for a total drying time of about 45 minutes resulted in a completely dried agglomerated mixture. The dried slurry was then ground in a mortar and pestle to produce a PCMX/clay agglomerate having a particle size of below about 850 microns.

EXAMPLE 2

To evaluate the antibacterial effects provided to laundered fabrics in accordance with the present invention fabrics were washed in a Maytag washing machine using the protocol described below.

Washing Protocol

Tests were conducted at a water temperature of 77° F.; a water hardness of 150 ppm; a water volume of 45 liters (12 gallons); and a detergent concentration of 7.0 g/liter. For each of four comparative tests, 315 grams of powdered laundry detergent was used (7.0 g/l×45 liters=315 g) and to provide 1% of PCMX in the product formula using an agglomerate in accordance with the invention, 34.62 grams of the PCMX/bentonite carrier described in Example 1 was added and mixed with the 315 grams of powdered detergent.

The fabric load consisted of 10"×10" fabric swatches of the following four fabrics: cotton percale; 65% Dacron/35% Cotton; Dacron Single Knit, and Terry Cotton. The total weight of these swatches per washing load was about ½ lb.

The washing was conducted as follows: after filling the washer with water, the detergent product was added and agitated for 2 minutes, following which the swatches were added and washed for 10 minutes. About 500 ml of the wash solution was then taken as a sample for analysis of the level of PCMX. The washing machine was then allowed to drain and continue through the rest of the spin cycle, rinse cycle and final spin cycle.

Two replicates of each fabric were dried in an electric clothes dryer for 45 minutes, or until dry.

Four detergent compositions were tested as defined below:
(1) Control A; (2) Control A with 1% PCMX; (3) Control A with 1% PCMX/clay agglomerate; (4) Control A with 1% PCMX/clay agglomerate+PEDT. Detergent compositions (1) and (2) are outside the invention; detergent compositions (3) and (4) are in accordance with the invention.

Control A is a commercial powder detergent having the following composition.

| Control A | |
|---|---|
| Component | Weight Percent |
| Water | 15.1 |
| Dodecyl benzene sulfonate (linear) | 24.3 |
| Silicate (1:2.35) | 10.4 |
| Pentasodium tripolyphosphate | 12.2 |
| Soda Ash | 4.9 |
| Anhydrous sodium sulfate | 29.2 |
| Sodium polyacrylate | 2.2 |
| Enzyme | 0.7 |
| Adjuvants (color, perfume, etc.) | Balance |
| Total | 100.0 |

Detergent composition (2) was prepared by adding 1% by weight of PCMX powder to Control A.

Detergent composition (3) was prepared by adding 34.6 grams of the PCMX/bentonite agglomerated carrier described in Example 1 to 315 grams of powdered Control A thereby providing 1% of PCMX and 10% bentonite in the final composition.

Detergent composition (4) was prepared by adding 2%, by weight, of melted PEDT (pentaerythritol ditallowate) to the PCMX/bentonite agglomerated carrier described in Example 1, followed by mixing, drying and regrinding of the agglomerate mixture to a particle size below about 850 microns. The resulting PCMX/PEDT/bentonite agglomerated carrier in a weight ratio of 1:2:10 was added to 315 grams of Control A detergent composition in an amount (41 grams) to provide 1% PCMX in the final detergent composition.

Protocol for Measurement of PCMX on Fabric

The level of deposition of PCMX antibacterial agent on cotton percale and 65/35 Dacron/Cotton fabrics was measured using an HPLC analyzer (High Performance Liquid Chromatography).

The PCMX was extracted from the fabric swatches by first placing small pieces of fabric cut from an initial piece of fabric of about 3"×4" into a 250 ml beaker, followed by the addition of 80 ml of acetonitrile. The beaker was stirred for about 10 minutes and the pieces of fabric were then removed from the beaker. The solution in the beaker was allowed to evaporate to about 5 ml.

The solution was then transferred to a 10 ml volumetric flask. The 250 ml beaker was rinsed with two 1 ml portions of acetonitrile and the acetonitrile was then added to the 10 ml flask. The flask was brought to 10 ml volume with deionized water, and the sample was ready for analysis by HPLC.

The measurements are shown below.

TABLE 1

| PCMX Antibacterial Agent Deposition on Fabric | | |
|---|---|---|
| Detergent Composition | Cotton Percale | 65/35 Dacron/Cotton |
| (1) Control A | 0.2 ppm | 0 ppm |
| (2) Control A with 1% PCMX | 2.1 ppm | 2.7 ppm |
| (3) Control A with PCMX/Clay Agglomerate (1% PCMX) | 12.8 ppm | 12.6 ppm |
| (4) Control A with PCMX/Clay/PEDT Agglomerate (1% PCMX) | 13.7 ppm | 13.6 ppm |

As noted in Table 1, the incorporation of the agglomerated carrier of the invention in compositions (3) and (4) resulted in significantly enhanced deposition of PCMX antibacterial agent on the laundered fabrics.

EXAMPLE 3

The following experiment was conducted to measure the level of PCMX in the wash solution and the amount deposited on laundered fabrics in accordance with the present invention. The following washing protocol was followed.

Washing Protocol

The washing protocol described in Example 2 was followed using the PCMX/bentonite carrier described in Example 1 with two exceptions: (1) the level of PCMX provided to the product formula was 0.3%, by weight; and (2) the fabric swatches were line dried instead of in an electric dryer.

The four detergent compositions which were used in the comparative tests are defined below:
(1) Control A; (2) Control A with 0.3% PCMX; (3) Control A with 0.3% PCMX/Clay agglomerate; and (4) Control A with 0.3% PCMX/Clay/PEDT agglomerate.

Detergent compositions (1) and (2) are outside the invention; detergent compositions (3) and (4) are in accordance with the invention.

Control A is defined in Example 2.

Detergent composition (2) was prepared by adding 0.3% by weight of PCMX powder to Control A.

Detergent composition (3) was prepared by adding and mixing 10.4 grams of the PCMX/bentonite carrier of Example 1 to the 315 grams of powdered detergent Control A to provide 0.3% by weight of PCMX.

Detergent composition (4) was prepared by adding 0.6%, by weight, of melted PEDT to PCMX/bentonite agglomerated carrier followed by mixing, drying and regrinding of the agglomerated mixture to a particle size below about 850 microns. The resulting PCMX/PEDT/bentonite agglomerated carrier in a weight ratio of 1:2:10 was added to 315 grams of Control A in an amount (12.3 grams) to provide 0.3% by weight of PCMX in the final detergent composition.

Protocol for Measurement of PCMX in the Wash Solution

After washing the stained swatches for 10 minutes with each of the four detergent compositions in accordance with the washing protocol defined above, a sample of the wash solution was taken for analysis of the level of PCMX.

To 12 ml of the wash solution there was added 12 ml of acetonitrile in a 25 ml flask. The level of PCMX was measured using an HPLC analyzer.

The measurements are shown in Table 2 below:

TABLE 2

PCMX Antibacterial Agent Concentration in the Wash Solutions

| Detergent Composition | PCMX Concentration (ppm) |
|---|---|
| (1) Control A | 0 |
| (2) Control A with 0.3% PCMX | 2.7 |
| (3) Control A with PCMX/Clay Agglomerate (0.3% PCMX) | 15.6 |
| (4) Control A with PCMX/Clay/PEDT Agglomerate (0.3% PCMX) | 11.1 |

As noted in the Table, the incorporation of the agglomerated carrier of the invention in Compositions (3) and (4) provided a significantly higher concentration of PCMX antibacterial agent in the wash solution relative to the use of detergent compositions outside the invention.

What is claimed is:

1. A method for preparing a particulate agglomerated carrier which is an agglomerate of a smectite-type clay and an antibacterial agent, which carrier is suitable for use in admixture with a laundry detergent composition or as an additive to a wash solution separate from any detergent composition, and which carrier is capable of depositing an effective amount of said antibacterial agent on laundered fabrics, comprising the steps of:
    (a) providing (i) finely divided particles of said smectite-type clay, and (i) an antibacterial agent which is normally solid at ambient temperature;
    (b) heating said particles of smectite-type clay and said antibacterial agent to a temperature above ambient;
    (c) agglomerating said particles of smectite-type clay while at a temperature above ambient with a melt of said antibacterial agent to form an agglomerated mixture; and
    (d) reducing the size of the agglomerated mixture of (c) to form particles in a range desired for said particulate agglomerated carriers wherein a higher aliphatic $C_{12}$–$C_{22}$ ester of pentaerythritol or a higher $C_{12}$–$C_{22}$ ester of an oligomer of pentaerythritol is further included in the agglomerated mixture of step (c).

2. The method in accordance with claim 1 wherein said agglomerated carrier is devoid of any plastic resin.

3. The method in accordance with claim 2 wherein said antibacterial agent does not include a metal ion or alkali metal ion.

4. The method in accordance with claim 1 wherein the weight ratio of clay to antibacterial agent is from about 15:1 to about 5:1.

5. The method in accordance with claim 4 wherein the weight ratio of clay to antibacterial agent is about 10:1.

6. The method in accordance with claim 1 wherein the smectite-type clay is bentonite.

7. The method in accordance with claim 1 wherein the antibacterial agent is PCMX (para chloro meta xylenol).

8. The method in accordance with claim 1 wherein the antibacterial agent is Triclosan (2,4,4'trichloro-2'hydroxydiphenyl ether).

9. A process for depositing an effective amount of an antibacterial agent on laundered fabrics comprising
    (a) dispersing the particulate agglomerated carrier produced in accordance with claim 1 in the wash water or rinse water of a washing machine or hand washing operation; and
    (b) contacting the fabrics to be laundered with said particulate agglomerated carrier in the wash water or rinse water whereby at least a partial amount of the antibacterial agent in said carrier is deposited on the laundered fabrics.

10. A process in accordance with claim 9 wherein said agglomerated carrier is devoid of any plastic resin.

11. A process in accordance with claim 9 wherein the weight ratio of clay to antibacterial agent is from about 15:1 to about 5:1.

12. A process in accordance with claim 11 wherein the weight ratio of clay to antibacterial agent is about 10:1.

13. A process in accordance with claim 9 wherein the smectite-type clay is bentonite.

14. A process in accordance with claim 9 wherein the antibacterial agent is PCMX (para chloro meta xylenol).

15. A process in accordance with claim 9 wherein the agglomerated carrier further includes a higher aliphatic $C_{12}$–$C_{22}$ ester of pentaerythritol or a higher $C_{12}$–$C_{22}$ ester of an oligomer of pentaerythritol.

16. A laundry detergent composition comprising
    (a) at least one surfactant selected from the group consisting of anionic and nonionic surfactants; and
    (b) a particulate agglomerated carrier produced in accordance with claim 1.

17. A laundry detergent composition in accordance with claim 16 wherein the weight ratio of clay to antibacterial agent in the agglomerated carrier is from about 15:1 to about 5:1.

18. A laundry detergent composition in accordance with claim 16 wherein the smectite-type clay in the agglomerated carrier is bentonite.

* * * * *